United States Patent
Drouillard

(10) Patent No.: US 9,265,260 B1
(45) Date of Patent: Feb. 23, 2016

(54) SYSTEMS AND METHODS FOR USING LIGHT ENERGY TO FACILITATE PENETRATION OF SUBSTANCES IN PLANTS

(71) Applicant: GPD Technologies, LLC, Sharpsburg, GA (US)

(72) Inventor: Gregory P. Drouillard, Sharpsburg, GA (US)

(73) Assignee: GPD TECHNOLOGIES LLC, Sharpsburg, GA (US)

( * ) Notice: Subject to any disclaimer, the term of this patent is extended or adjusted under 35 U.S.C. 154(b) by 0 days.

(21) Appl. No.: 14/551,902

(22) Filed: Nov. 24, 2014

Related U.S. Application Data

(60) Provisional application No. 61/976,051, filed on Apr. 7, 2014.

(51) Int. Cl.
*A01N 59/00* (2006.01)
*A01N 55/02* (2006.01)
*A01N 55/04* (2006.01)
*A01N 37/00* (2006.01)
*A01N 59/16* (2006.01)
*A01N 41/12* (2006.01)
*C05F 11/00* (2006.01)

(52) U.S. Cl.
CPC ............... *A01N 59/16* (2013.01); *A01N 41/12* (2013.01); *C05F 11/00* (2013.01)

(58) Field of Classification Search
None
See application file for complete search history.

(56) References Cited

U.S. PATENT DOCUMENTS

| | | | |
|---|---|---|---|
| 6,172,328 B1 * | 1/2001 | Jones et al. | 219/121.68 |
| 6,180,914 B1 | 1/2001 | Jones | |
| 6,508,785 B1 | 1/2003 | Eppstein | |
| 6,527,716 B1 | 3/2003 | Eppstein | |
| 7,758,561 B2 | 7/2010 | Eppstein | |
| 2003/0191458 A1 | 10/2003 | Diamond | |
| 2005/0210744 A1 | 9/2005 | Watanabe | |
| 2007/0218556 A1 | 9/2007 | Harris | |
| 2009/0306576 A1 | 12/2009 | Bragagna | |
| 2013/0259954 A1 | 10/2013 | Masaoka | |
| 2014/0024857 A1 | 1/2014 | Alves De Souza | |

FOREIGN PATENT DOCUMENTS

| | | | |
|---|---|---|---|
| CA | 2276312 | | 7/1998 |
| DE | 1273896 | * | 12/1965 |
| EP | 2681997 A1 | | 8/2014 |
| WO | 2010004581 A2 | | 1/2010 |
| WO | 2013148677 A1 | | 10/2013 |

OTHER PUBLICATIONS

Sood, Preeti et al, Laser Etching: A Novel Technology to Label Florida Grapefruit, Hortechnology, Jul.-Sep. 2009 19 (3), pp. 504-510.

Etxeberria, Ed et al, The Anatomy of a Laser Label, Florida State Horticulture Society, 2009, 122:347-349.

* cited by examiner

*Primary Examiner* — Alton Pryor
(74) *Attorney, Agent, or Firm* — Fish & Tsang LLP

(57) ABSTRACT

Systems and methods are disclosed for delivering a substance into a plant. The systems and methods include a light energy that is applied to a first area on the plant to create a first indentation. The first indentation can be a minor incision or a rupture of a portion of the first area. Once the first indentation is created, a first dosage of the substance is applied to the first area in an amount effective to promote a biological response of the plant. It is contemplated that at least a portion of the substance is absorbed by the plant via the first indentation.

20 Claims, 13 Drawing Sheets

SYSTEMS AND METHODS FOR USING LIGHT ENERGY TO FACILITATE PENETRATION OF SUBSTANCES IN PLANTS

This application claims priority to U.S. Provisional Application Ser. No. 61/976,051, filed Apr. 7, 2014, the entire content of which is incorporated herein by reference. All extrinsic materials identified herein are incorporated by reference in their entirety. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is devices and methods for delivering substances to plants.

BACKGROUND

The background description includes information that may be useful in understanding the present invention. It is not an admission that any of the information provided herein is prior art or relevant to the presently claimed invention, or that any publication specifically or implicitly referenced is prior art.

Plant pathogens pose a unique challenge to the plant industry. The failure to control pathogens can result in significant crop losses. For example, Huanglongbing (hereinafter "HLB") or Citrus greening disease is a serious threat to citrus production and an HLB infection can result in the loss of many trees.

Some have proposed methods of mitigating the damages of HLB using spray treatments. For example, Masaoka (US 2013/0259954) proposes using a liquid treatment containing Fe ions and at least some Fe ions in the form of $Fe^{2+}$ ions. The liquid treatment can be sprayed onto leaves of citrus trees or poured on the roots of citrus trees that are infected by Citrus greening disease. In another example, Borras Hidalgo (EP 2681997) discloses a method of treating HLB through simultaneous activation of genes related to the route of salicylic acid, jasmonic acid/ethylene and hypersensitive response. Similar to Masaoka, the treatment can be applied via spray.

While some methods have disclosed spray treatments, other methods have also been used to delivery treatment to plants. For example, De Souza (US 2014/0024857) discloses using a cysteine amino-acid compound to control HLB by aiming to disrupt bacterial clusters in the phloem of the affected plant. The cysteine amino-acid compound can be applied as a drench (i.e., flooding a small area near the plant) or as a fertilizer in an encapsulated form. In another example, Wang (WO 2013/148677) discloses using SecA inhibiting compounds to affect protein translocation and potential signal peptide dependent virulence factors of *Candidatius Liberibacter asiaticus* (CLas), which is a causal agent of HLB. Compounds can be applied by conventional methods, such as dusting, sprinkling, brushing, dipping, smearing, impregnating, injection into the vascular system, and application to the root system.

Control of CLas in mature field trees using antimicrobial substances can be a promising tool in the fight against HLB. However, it is important to note that the success of antimicrobial treatments is intimately dependent on factors other than the efficacy of the antimicrobial agent itself. For example, two factors that affect the success of antimicrobial treatments include: (i) degree of antimicrobial penetration into the plant, and (ii) percent of uptake by phloem cells.

The problem with some of the methods described above is that the penetration of substances into the aerial parts of a plant is severely hindered by the presence of protective layers such as the cuticle (wax/cutin) on leaves and bark on stems. Although the primary functions of these protective covers are to guard against invading pests and to minimize water loss, the cuticle and bark also make formidable protective shields rendering penetration of externally supplied substances (e.g., spraying, drenching, sprinkling, etc.) virtually impossible.

Consequently, penetration of externally supplied substances into leaves is typically possible only through the stomata openings (found only on the abaxial side of citrus leaves) and through occasional cracks on the cuticle itself. Nevertheless, the collective surface area of stomatal openings that would allow for penetration of externally supplied solutions into the leaf is minimal, even under optimum conditions, since stomata often close under a variety of biotic and abiotic situations. Similarly, the bark, a complex tissue made up of dead suberized cork cells to the exterior and phloem cells to the interior, has very limited permeability through the cell wall fibrous material. Thus, the limited permeability of the cuticle and bark can be costly because more treatment may be needed to ensure enough absorption for the effective treatment of the plant. Additionally, using copious amounts of treatments can lead to pollution problems, which can greatly reduce soil quality.

Other methods of the delivery of a substance are disclosed in Eppstein (CA 2276312) and Watanabe (US 2005/0210744).

Thus, there is still a need for more efficient devices and methods for delivering substances to plants.

SUMMARY OF THE INVENTION

The inventive subject matter provides apparatus, systems and methods in which light energy can be used to enhance the penetration of a substance in plants. This is accomplished by applying a light energy to a first portion of a plant to create an indentation. Once the indentation is created, a first dosage of a substance can be applied to the plant.

In one aspect, a plant having a disease can be treated. The plant has an infected site, which is typically within the plant (e.g., phloem, root). A light energy is applied to a treatment area on the plant to create a first indentation. In typical embodiments, the treatment area is distal from the infected site. Moreover, the indentation can be a rupture, an ablation, a disruption or a minor incision in the treatment area. Once the indentation is created, a first dosage of a substance is applied to the treatment area in an amount effective to induce a therapeutic response in the infected site.

It should be appreciated that treating a plant does not require a complete cure of the plant from the disease, but can also include a reduction in the state of the disease or a reduction in a symptom of the disease. Moreover, treatment of a plant can also include providing nutrients and supplements to enhance the health of the plant.

In contemplated embodiments, the step of applying a light energy includes creating an indentation pattern. The indentation pattern can be a single dot, a plurality of dots, a single line, a plurality of lines, a continuously bending line (e.g., swirls, random curves, etc.), a plurality of continuously bending lines, and combinations thereof. It is contemplated that the indentation pattern can influence the amount of the first dosage of the substance that is required to be effective to induce a therapeutic response. Furthermore, the first indentation can have a diameter of approximately 100-500 µm. Thus, it should be appreciated that various indentation depths, widths, lengths, surface areas, and patterns can be used to promote a therapeutic response in a minimally invasive manner.

In contemplated embodiments, the step of applying a light energy is before the step of applying a first dosage. However, it should be appreciated that the reverse order can also be performed to treat a plant. A predetermined time can be used to regulate the performance of such steps to ensure effective uptake of the substance into the plant via the first indentation. For example, the step of applying a light energy and the step of applying a first dosage can be performed in less than 1 hour, less than 30 minutes, or even less than 1 minute from one another.

As briefly mentioned above, the infected site can be in a phloem. In such embodiment, suitable treatment areas include a surface of at least one of a leaf, a stem and a bark of the plant. For example, a plant can be a citrus tree having HLB. The citrus tree having HLB has an infected site of the phloem. To treat the citrus tree, light energy can be applied to create a first indentation on a treatment area, which can include at least one of a leaf, a steam and a bark. Once the indentation is created, a first dosage of a substance (e.g., an antimicrobial substance) can be applied to the treatment area in an amount effective to induce a therapeutic response (e.g., reduce a symptom of HLB). It should be appreciated that the first indentation can comprise a rupture of a cuticle on the leaf to allow introduction of the substance.

While the embodiments described above have discussed a light energy creating a first indentation, it is contemplated that the step of applying the light energy to the treatment area can include creating a second indentation. With a second indentation, the first dosage of the substance can be beneficially received by the first and second indentation. Thus, additional indentations are contemplated so long as the amount of indentations created is minimally invasive to prevent or reduce damage to the plant.

In order to reduce the risk of damage to the plant, the inventor has contemplated applying a wax to the treatment area in an amount effective to seal the first indentation after the steps of applying the light energy to the treatment area and applying the first dosage of a substance to the treatment area are complete. As a further step of precaution an antifungal spray can be applied to the treatment area.

The treatment area and the infected site can be in distinct plant systems. For example, the treatment area can be in the dermal system of the plant (e.g., cuticle, cork) while the infected site can be in the vascular system of the plant (e.g., phloem). In addition, as briefly discussed above, the treatment area and infected site can be distal. As used herein, "distal" means situated away from. In some instances, distal may refer to a physical distance between the treatment area and the infected area, for example, a distance of between 0.01 cm to 100 cm, more preferably, between 0.05 cm to 50 cm, and most preferably, between 0.1 cm to 25 cm. In other instances, distal may refer to a distance between treatment area and infected site in terms of a systemic pathway. For example, the treatment area and the infected site are distal by one to two layers of a plant epidermis or one to two layers of bark tissues. In addition, distal could refer to a systemic distance that crosses multiple systems (e.g., dermal system, vascular system, ground system).

In another aspect, it is contemplated that a first substance is delivered to a first site in a plant. In such embodiment, a light energy is applied to a second site located on a plant surface to create a first disruption. The first disruption can be a rupture, an ablation, a disruption or a minor incision. The first site (e.g., phloem, xylem) and the second site (e.g., cuticle, cork) can be different in kind. In other words, the first site and the second site can be different plant systems (e.g., dermal system, vascular system) or different plant tissues. Once a disruption is created, a first dosage of the first substance can be applied to the second site in an amount effective to promote uptake of the first substance and delivery to the first site via the first disruption. The first dosage and first disruption are sufficient to achieve a biological response.

The first substance can comprise at least one of an antimicrobial, a pesticide, a fertilizer, an herbicide, a fungicide, or any other compound that provides a desired response. While a first dosage of the first substance may be beneficial for a biological response, it is contemplated that a second dosage of either the first substance or a second substance can be applied after the first dosage. The second substance can include at least one of an antimicrobial, a pesticide, a fertilizer, an herbicide and a fungicide.

The plant includes a tree, a row crop, a bush crop and an ornamental plant. Furthermore, as a precautionary measure, a wax can be applied to the second site in an amount effective to seal the first disruption after the steps of applying the light energy to the second site and applying the first dosage of the substance to the second site.

In yet another aspect, a compound can be delivered to a living plant. In such embodiment, a light energy is applied to a first portion of the plant to create a first indentation. Thereafter, a first dosage of the compound is applied to the first superficial indentation in an amount effective to induce a biological response.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It has been discovered that light energy can be used to enhance the penetration of a substance in plants. This is accomplished by applying a light energy to a first portion of a plant to create an indentation. Once the indentation is created, a first dosage of a substance can be applied to the plant. It should be appreciated that at least a portion of the first dosage can penetrate the plant via the indentation. Thus, and with respect to some plants, the obstacles imposed by the cuticle and bark are overcome by the creation of the indentation for the delivery of the substance.

Figure 1:
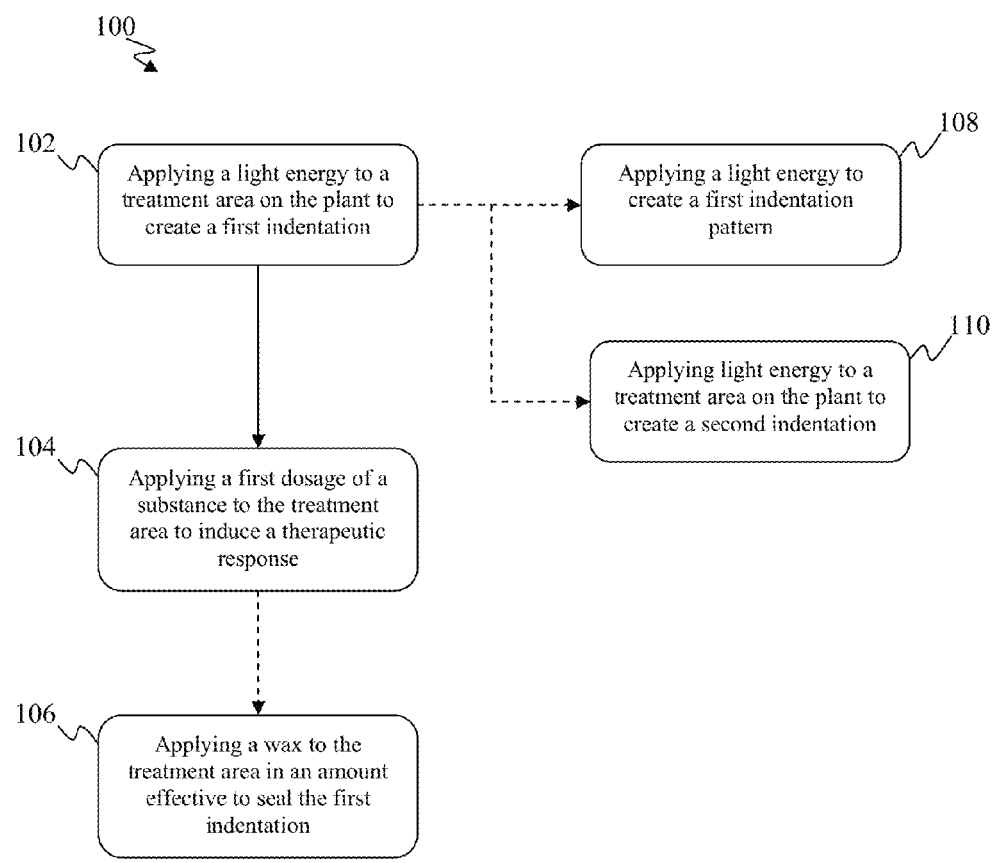
FIG. 1 is a schematic of a method of treating a plant having a disease in an infected site of the plant.

FIG. 1 shows a schematic of a method 100 for treating a plant having an infected site. Method 100 comprises a step 102 of applying a light energy to a treatment area on the plant to create a first indentation. Typically, the treatment area is distal from the infected site. In another step 104, a first dosage of a substance is applied to the treatment area in an amount effective to induce a therapeutic response in the infected site. Suitable therapeutic responses can include a complete cure of a disease causing the infected area, a reduction in the infected area, a reduction in a symptom of the disease causing the infected area, or a health stimulant.

In preferred embodiments, step 102 of applying the light energy to the treatment area occurs prior to step 104 of applying the first dosage of the substance. However, it is contemplated that the reverse order can be performed to treat a plant whereby step 104 occurs prior to step 102. Regardless of the order in steps 102 and 104, a predetermined time can be used to determine when each step is to be completed with respect to one another. For example, step 102 and step 104 could be completed within less than 1 hour, more preferably less than 30 minutes, and most preferably within 1 minute of one another. Therefore, uptake of the substance via the first indentation can be enhanced by performing steps 102 and 104 within the predetermined time. If the substance is a drug that has a delayed time of therapeutic activity, the time that passes between performing steps 102 and 104 can be adjusted to compensate for the delayed therapeutic activity of the substance.

It is further contemplated that the parameters of the first indentation (e.g., size, shape, depth, pattern, etc.) can influence the therapeutic response in the infected area. An additional step 108 of applying a light energy can include creating an indentation pattern. Suitable indentation patterns can be as simple as one dot or one line. Indentation patterns could be more complex and may include a plurality of dots, lines, continuously curved lines, or a combination thereof. It should be appreciated that indentation patterns can influence the uptake of the substance into the plant by providing different dimensional shapes and areas for absorption. It is contemplated that method 100 could include an additional step 110 of applying the light energy to create a second indentation, or any number of additional indentations.

Method 100 can also include an additional step 106 of applying a wax to the treatment area in an amount effective to seal the first indentation and any additional indentations. It is contemplated that the step of applying the wax is performed after the steps of applying the light energy to the treatment area and applying the first dosage of a substance to the treatment area. In this fashion, the first indentation can be sealed from the outside environment to prevent harmful contaminants from accessing the plant through the first indentation. In addition, the wax reduces the amount of perspiration of the substance to help its absorption into the plant.

FIGS. 2A-2F shows a cross section of a plant 200, which has an infected site 206. The figures illustrate a method of treating the infected site 206. Plant 200 could comprise any type of plant life, including a tree, vines, forage, perennial crops, row crops, bush crops, an ornamental plant, annual plants, and grasses. In one example, plant 200 is a citrus tree. Thus, it should be noted that the methods disclosed herein could be applied to all different plant types to improve the delivery of a substance into the plant. It should also be noted that while the methods disclosed thus far relate to treating diseased plants, the methods herein can also be applied to healthy plants for preventive care or to promote overall health (e.g., fertilizer application).

A plant can have a plurality of infected sites. Infected site 206 can have an area affected by various known diseases/pathogens. For example, infected site 206 can be an area in a plant affected by HLB, Citrus Tristeza Virus (CTV), Citrus Variegated Chlorosis (CVC), citrus canker, Pierce's disease. While FIG. 2A shows infected site 206 within plant 200, it is contemplated that infected site 206 can reside on the outside surface of plant 200.

Figure 2A:
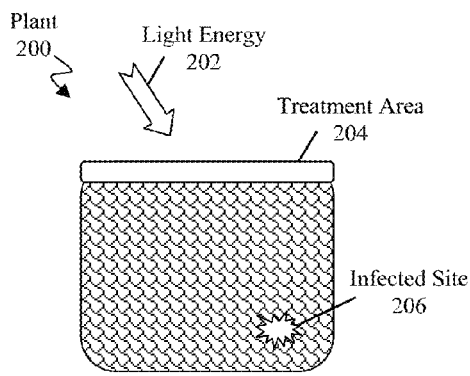
FIGS. 2A-2F are perspective views of an embodiment showing delivery of a first substance from a treatment area to an infected site.

FIG. 2A shows a light energy 202 being applied to a treatment area 204 of plant 200. Treatment area 204 is typically on a surface of plant 200. However, it is contemplated that treatment area 204 can also be within plant 200 (i.e., beyond the outer epidermis). Treatment area 204 can be a region of a plant or a specific organ of a plant (e.g., leaf, bark, stem, etc.). In addition, treatment area 204 can comprise a targeted coverage area of a plant. For example, treatment area 204 can comprise a maximum of 25% of the surface area of the plant (e.g., leaf, stem, trunk, etc.), and more preferably a maximum of 20% of the surface area of a plant.

Treatment area 204 is typically distal from infected site 206. For example, treatment area 204 can be a surface of at least one of a leaf, a stem, and a bark, while the infected site is in a phloem of plant 200. In particular, treatment area 204 could be in the dermal system of plant 200 while the infected site 206 could be in the vascular system of plant 200. Therefore, it is contemplated that the treatment area and the infected site are in distinct plant systems (e.g., dermis, vascular, ground).

Figure 2B:
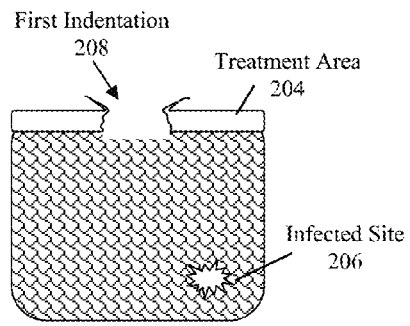

Light energy 202 is used to create a first indentation 208 as shown in FIG. 2B. Co-invented U.S. Pat. Nos. 5,660,747 and 5,897,797, and U.S. Pat. Pub. 2005/0226975 describe various techniques for etching the skin of produce using energy from a $CO_2$ laser. It is contemplated that the present inventive subject manner may employ some of the techniques in these references, or modifications thereof, in combination with suitable operational parameters, to accomplish the objectives of the present inventive subject matter. For example, light energy 202 could comprise a $CO_2$ laser that is configured with suitable parameters (e.g., size/diameter, quality, spatial intensity distribution, divergence, wavelength, etc.) that are sufficient to produce the desired indentation in a particular treatment surface (e.g., leaf). In some embodiments, suitable parameters for light energy 202 (e.g., a laser) include a wavelength having about 10 micrometers (e.g., 10.6 micrometers) and a power output range between 20-90% at 30-2000 microseconds. It is contemplated that the power output of light energy 202 can range from 10-100 watts. It should be appreciated that the suitable parameters can be adjusted in real-time to accommodate various environmental factors that could affect light energy 202.

As treatment area 204 can comprise different parts of plant 200 (e.g., leaf and bark), it is contemplated that different parameters of light energy 202 can be used for different parts of plant 200. For example, light energy 202 applied to a bark to create an indentation typically requires more power and dwell than light energy 202 applied to a leaf to create an indentation. Suitable power settings for applying light energy 202 to a bark are in the range of 80-90% power at a dwell of 1200-2000 microseconds depending on the age of plant 200. On the other hand, grasses would typically require less power in the range of 20-50% power at a dwell of 30-120 microseconds.

As discussed above, suitable parameters for light energy 202 can vary depending on environmental factors, amongst other things. To better operate a real-time system that adjusts light energy 202, it is contemplated that a control system (e.g., a feedback loop) having sensors are integrated with light energy 202. The sensors can be used to detect various parameters affecting the application of light energy 202, such as the different parts of plant 200 (e.g., bark vs. leaf), weather, age of plant 200, depth and size of first indentation 208, and the distance from the light energy source and treatment area 204. Upon obtaining sensor data on various parameters, the control system adjusts light energy 202 to create an indentation. For example, a sensor can detect that treatment area 204 is part of the bark of plant 200 and adjust the power settings of light energy 202 to create an indentation, and at a subsequent point in time the sensor can detect that treatment area 204 is on the surface of grass and adjust the power settings by reducing power of light energy 202 to create an indentation. In another example, light energy 202 can have a default setting (e.g., power setting to create indentation on a leaf of plant 200) and, upon sensing another part (e.g., stem, bark) of plant 200, control system can adjust light energy 202 to create an indentation before returning to the default setting. In yet another example, a sensor can be integrated within light energy 202 to determine whether first indentation 208 has reached a pre-determined tissue layer.

In contemplated embodiments, light energy 202 can be applied having the light energy source in contact with treatment area 204. However, in other more typical embodiments, light energy 202 can be applied having the light energy source at a distance from treatment area 204. For example, the light energy source can be between 4 to 14 inches (e.g., 7 inches) from treatment area 204. In another example, light energy 202 comprises a $CO_2$ laser and treatment area 204 is on a surface of a leaf whereby the distance between the $CO_2$ laser and the leaf is between 4 to 14 inches, and more preferably, 5 to 8 inches.

First indentation 208 is a removed or disrupted portion of treatment area 204. In contemplated embodiments, first indentation 208 comprises an opening through the treatment area 204. In other words, first indentation 208 extends through treatment area 204 to expose a surface underneath treatment area 204. For example, first indentation 208 can be a rupture, ablation, or disruption of a cuticle on the leaf. It should be appreciated that first indentation is intended to be minimally invasive to the plant. Therefore, typical diameters for first indentation 208 are approximately between 100-and 300 µm, and typically have a depth of approximately 50 µm.

It should be noted that first indentation 208 can have a greater or lesser depth, but the depth should generally not exceed 75 µm as it may destroy too many cells.

While first indentation 208 can extend through treatment area 204, it is also contemplated that first indentation 208 can extend partially through treatment area 204. In other words, first indentation 208 need not be a complete breach through treatment area 204 (e.g., the depth of first indentation 208 does not extend into the entire thickness of the cuticle). On the other hand, it is also contemplated that first indentation 208 can extend through various layers past treatment area 204. Preferably, first indentation 208 is configured to achieve maximum uptake of the substance while minimizing harm to the plant.

Figure 2C:
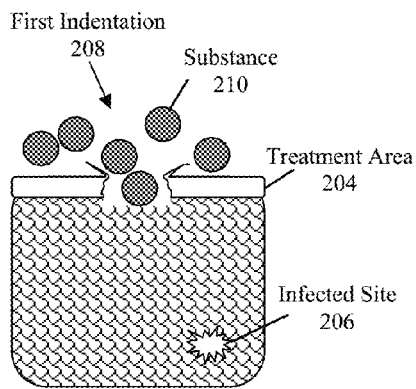

Once first indentation 208 is created, a first dosage of a substance 210 is applied to treatment area 204 as shown in FIG. 2C. Substance 210 can be applied to first indentation 208 using various methods, including spraying, dusting, sprinkling, brushing, smearing and drenching. Application of the first dosage could also be accomplished by introducing substance 210 into an irrigation system (e.g., sprinkler system) that delivers water to the plant. Using these application techniques, some of substance 210 enters first indentation 208. It is also contemplated that a more targeted application technique can be used to focus the application of substance 210 onto the area of first indentation 208.

Substance 210 is typically a substance to promote overall health or treatment of plant 200. In one embodiment, substance 210 can be an antimicrobial substance. Suitable antimicrobial substances include HLB treatment substances (e.g., liquid treatment containing Fe ions and at least some Fe ions in the form of $Fe^{2+}$ ions, cysteine amino-acid compound, SecA inhibiting compounds, etc.) and substances that treat other pathogenic diseases (e.g., Citrus Tristeza Virus (CTV), Citrus Variegated Chlorosis (CVC), citrus canker, Pierce's disease). Moreover, it is contemplated that substance 210 can be effective to control *Candidatius Liberibacter asiaticus*. Other suitable antimicrobial substances can also be applied using the enhanced delivery methods disclosed herein to treat plant pathogens.

While substance 210 can be effective to treat a plant, it is contemplated that substance 210 can be a pesticide, a fertilizer, an herbicide, a fungicide or a vitamin/supplement. Moreover, other substances can be applied to help support the overall health of the plant. Thus, it should be appreciated that the enhanced delivery methods disclosed herein are not limited by the type of substance that is applied.

In yet other embodiments, substance 210 could comprise a harmful chemical or compound configured to kill and eliminate the plant. In this manner, the inventive methods and devices can be used to selectively remove certain plants from a crop, such as to remove weeds, infected plants, older plants, etc. In such embodiments, first indentation 208 can be configured to optimize uptake without concern for being minimally invasive.

It is further contemplated that substance 210 are packaged into a variety of lipid soluble nano-particles. These nano-particles should provide for higher retention rates and for improved cuticle penetration. When combined with the use of light energy to create an indentation for the substance 210, penetration of nano-particles (or substances in solution) can be exceptionally enhanced.

Figure 2D:
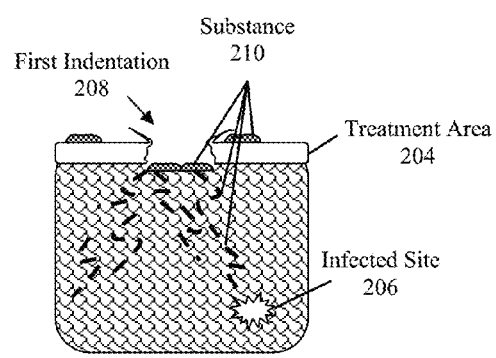

Typically, substance 210 is better absorbed through first indentation 208 as shown in FIG. 2D. Among the various reasons for the better absorption, it should be noted that substance 210 within first indentation 208 has a more direct path within plant 200 as opposed to substance 210 that is on the outer layer (i.e., outer surface of treatment area 204) of plant 200. It is preferred that the first dosage of substance 210 applied to treatment area 204 is in an amount effective to induce a therapeutic response in infected site 206.

Figure 2E:
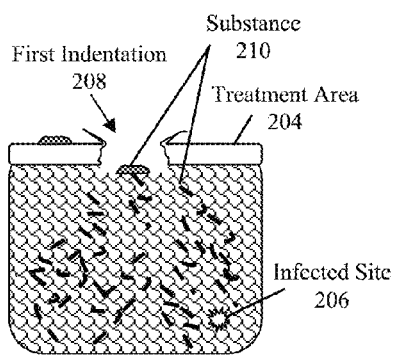

The therapeutic response in plant 200 can be in various manners. For example, the therapeutic effect can comprise a reduction in the infected site 206 as shown in FIG. 2E. In another example, the therapeutic response comprises reducing a symptom of a pathogen or completely curing a disease. In one embodiment, substance 210 is an antimicrobial substance and the therapeutic response comprises reducing a symptom of HLB.

It should be appreciated that substance 210 can also achieve a biological response. The biological response can comprise the therapeutic response in reducing a symptom of a pathogen or completely curing a disease. For example, when substance 210 comprises a biocide, it is contemplated that the desired biological response is to deter, render harmless, or exert a controlling effect on any harmful organism. In another example, when substance 210 comprises a fungicide, it is contemplated that the desired biological response is to kill or inhibit fungi or fungal spores. In yet another example, when substance 210 comprises a fertilizer, it is contemplated that the biological response is delivering plant nutrients essential to the growth of plants.

Figure 2F:
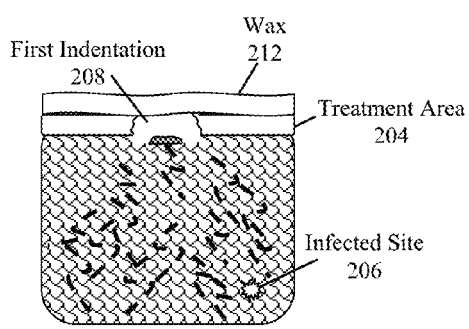

After creating first indentation 208 and applying substance 210, a wax 212 can be applied to treatment area 204 as shown in FIG. 2F. It should be appreciated that wax 212 has several benefits, including preventing pathogen or other harmful contaminants from entering first indentation, reducing water loss, and reducing perspiration of substance 210 from first indentation 208. Thus, water loss will be mainly localized and should not affect the overall tree water relations.

Figure 3A:
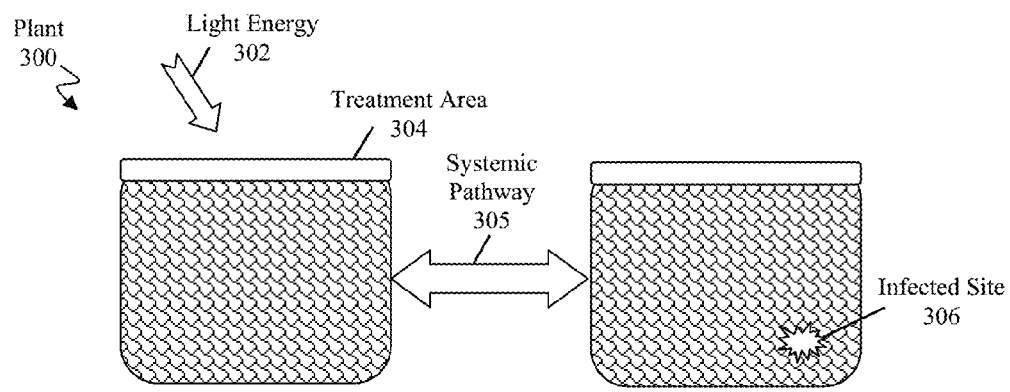
FIG. 3A-3F are perspective views of an embodiment showing delivery of a first substance from a treatment area to an infected site separated by a systemic pathway.
Figure 3B:
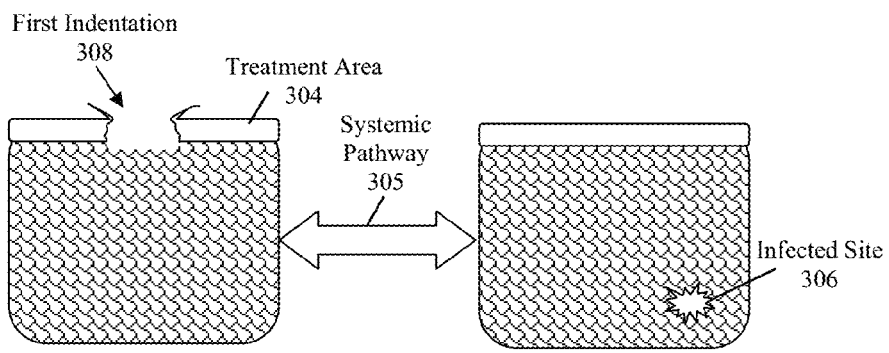
Figure 3C:
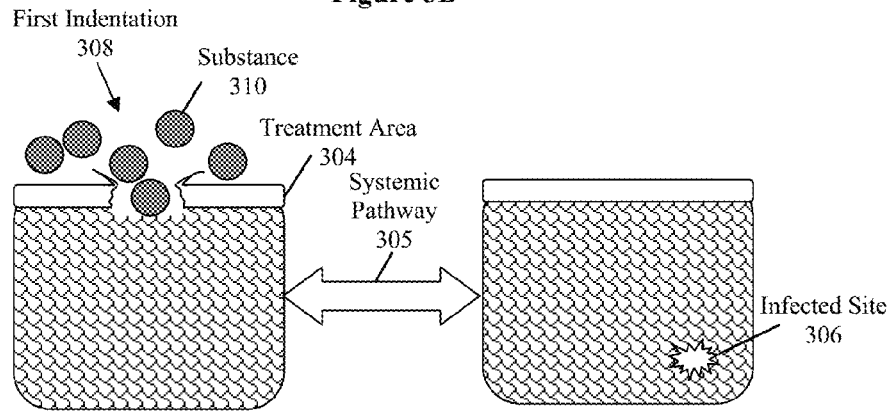

FIGS. 3A-3F shows a cross section of a plant 300, which has an infected site 306 that is distally located from a treatment area 304 across a systemic pathway 305. For example, treatment area 304 could be located on a first leaf and infected site 306 could be located on a second leaf, wherein the first leaf and separate leaf are located on different stems and/or branches. Light energy 302 is applied to treatment area 304 to create first indentation 308 as shown in FIGS. 3A-3B. Once first indentation 308 is created, a first dosage of substance 310 is applied to treatment area 304 as shown in FIG. 3C. As discussed above, substance 310 can be applied using various application methods.

Figure 3D:
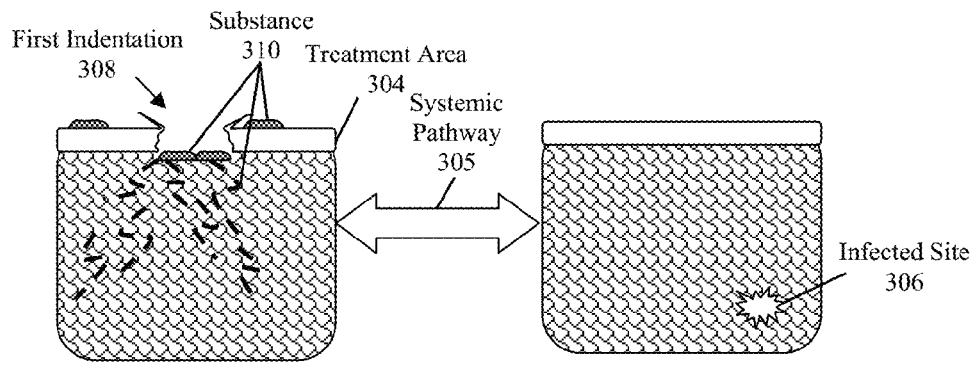

Substance 310 is absorbed by plant 300 through first indentation 308 as shown in FIG. 3D. While substance 310 has been introduced within plant 300, it should be noted that in some circumstances the infected site 306 is distal from treatment area 304, such that substance 310 is not immediately in contact with infected site 306 and is separated by a systemic pathway. Thus, first dosage of substance 310 and first indentation 308 should be configured (e.g., the quantity of first dosage, number of applications of dosage, size and depth of first indentation 308, percentage of coverage of first indentation 308, etc.) to allow for sufficient uptake and delivery of the substance 310 to the infected site 306 to achieve a therapeutic response at the infected site 306. It is contemplated that first indentation 308 is sized and dimensioned to receive approximately 10 nL of substance 310 for uptake.

Figure 3E:
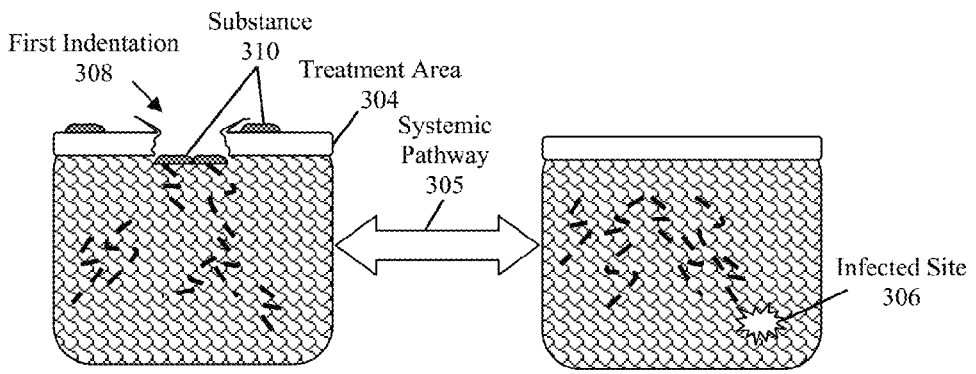
Figure 3F:
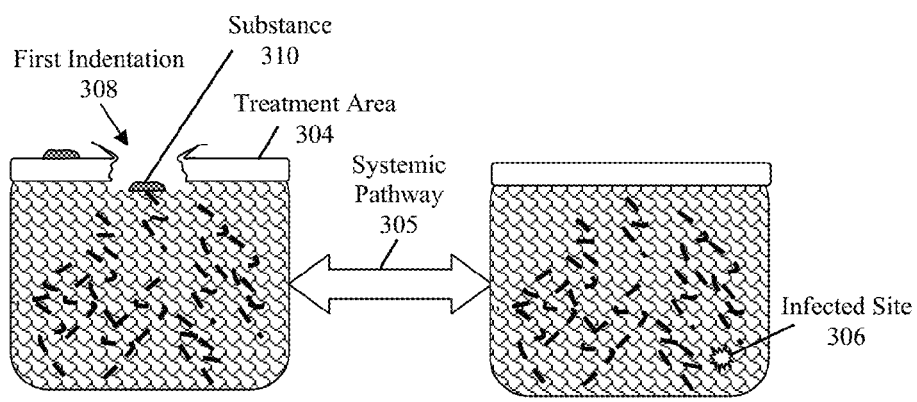
Figure 4A:
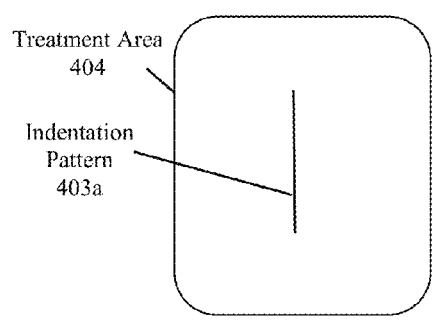
FIG. 4A-4D shows various embodiments of indentation patterns.
Figure 4B:
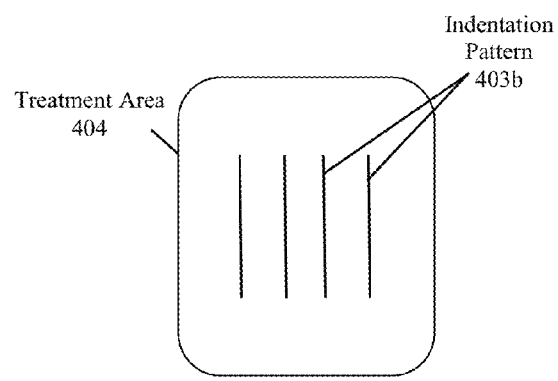
Figure 4C:
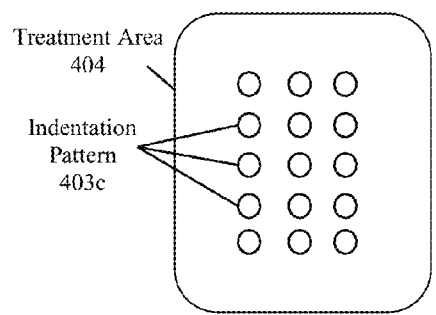
Figure 4D:
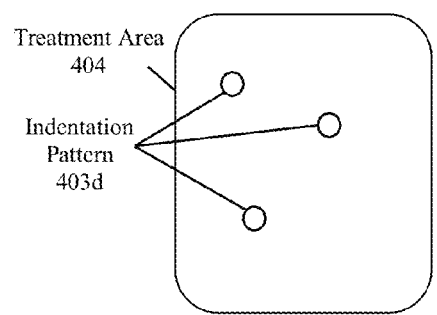

It is contemplated that substance 310 can travel through a systemic pathway 305 to arrive at infected site 306 as shown in FIG. 3E. While substance 310 is shown to be present in the area immediately adjacent to first indentation 308, it is contemplated that substance 310 does not have an effect (e.g., therapeutic or biological response) until it travels through systemic pathway 305. FIG. 3F shows first indentation 308 and substance 310 are sufficient to induce a therapeutic response, such as reducing the area of infected site 306.

As discussed above, a treatment area can have more than one indentation and can comprise an indentation pattern. FIGS. 4A-4D show a treatment area 404 that can have various indentation patterns 403a-d. For example, pattern 403a is a single solid line, pattern 403b comprises multiple solid lines, pattern 404c comprises a plurality of circular dots equally distanced from one another, and pattern 404d comprises a plurality of randomly spaced dots.

It should be recognized that a treatment area can span to various parts of a plant. For example, treatment area 404 can encompass the leaves, stems and the trunk of a plant. In another example, treatment area 404 can be limited to just one region or part of the plant (e.g., leaves, stems, bark, roots, etc.).

It should be appreciated that the indentations can vary in size and shape to account for differences in the absorption rate between various parts of the treatment area (e.g., the bark and the cuticle). For example, if it is determined that substances on an indentation on the bark are absorbed slower than substances on an indentation on the cuticle, then the superficial indentation on the bark can be larger to compensate for the slower absorption rate. Moreover, indentations can be created to promote capillary action of the antimicrobial substance.

Figure 5:
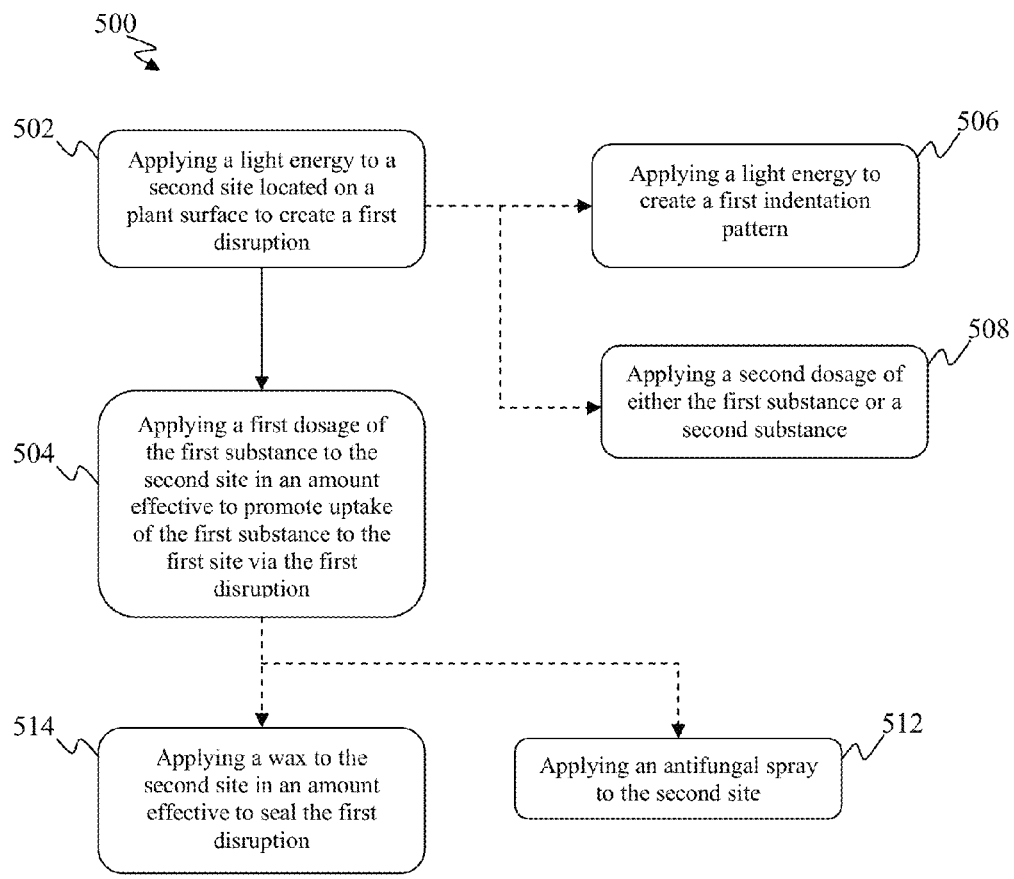
FIG. 5 is a schematic of a method of delivering a first substance to a first site in a plant.

In another aspect, a method 500 is contemplated for delivering a first substance to a first site (e.g., tissue, cell, infected site) in a plant as shown in FIG. 5. In step 502, a light energy is applied to a second site (e.g., epidermis of plant, treatment area) located on a plant surface to create a first disruption. In contemplated embodiments, the first site and the second site are different in kind (e.g., different tissues, cells, organs, systems of plant, distal). In another step 504, a first dosage of the first substance is applied to the second site in an amount effective to promote uptake of the first substance to the first site via the first disruption. A biological response is achieved using the first dosage and the first disruption.

The first dosage of the substance and the first disruption influence can influence the uptake of the substance and the corresponding biological response. The first disruption can be a rupture, an ablation, an indentation or a minor incision in the second site. By creating one or more disruptions on the second site, the amount of first dosage of the first substance can be reduced without affecting the biological response. However, while creating a plurality of disruptions provides increased sites for direct introduction of the substance into the plant, it is generally preferred that not more than 25% of the first site is covered with disruptions to avoid permanent damage to the plant. In some applications it may be advantageous to cover more than 25% of the first site with disruptions, especially when an additional step of waxing is applied after the disruptions to protect the plant from harmful substances.

As described in the embodiments above, the first substance comprises at least one of an antimicrobial, a pesticide, a fertilizer, an herbicide and a fungicide, each of which is capable of producing a biological response. For example, it is contemplated that first site can be a cuticle and the second site comprises at least one of a xylem and a phloem. In such instance, the first substance can be an antimicrobial and the biological response can be a reduction in a symptom of HLB.

In method 500, light energy can be used to create a first indentation pattern in step 506. Moreover, another step 508 can include adding another dosage of the first substance or applying a second substance. For example, a first dosage of the first substance can be applied, then after a pre-determined time period, a second dosage of the first substance can be applied. In another example, a first dosage of the first substance can be applied, then a first dosage of a second substance can be applied after a pre-determined time period.

The second substance can be an antimicrobial, a pesticide, a fertilizer, an herbicide and a fungicide. Additionally, the second substance can be a booster or a catalyst for the first substance to further activate the first substance. It is contemplated that the second substance can produce a second biological response, wherein the second biological response can be connected to the first biological response or distinct from the first biological response.

To prevent harm to the plant after the disruption is created, at least one of a step 512 of applying an antifungal spray to the second site and a step 514 applying a wax to the second site can be performed. In step 514, it is contemplated that wax is applied in an amount effective to seal the first disruption after the steps of applying the light energy to the second site and applying the first dosage of the substance to the second site.

Figure 6:
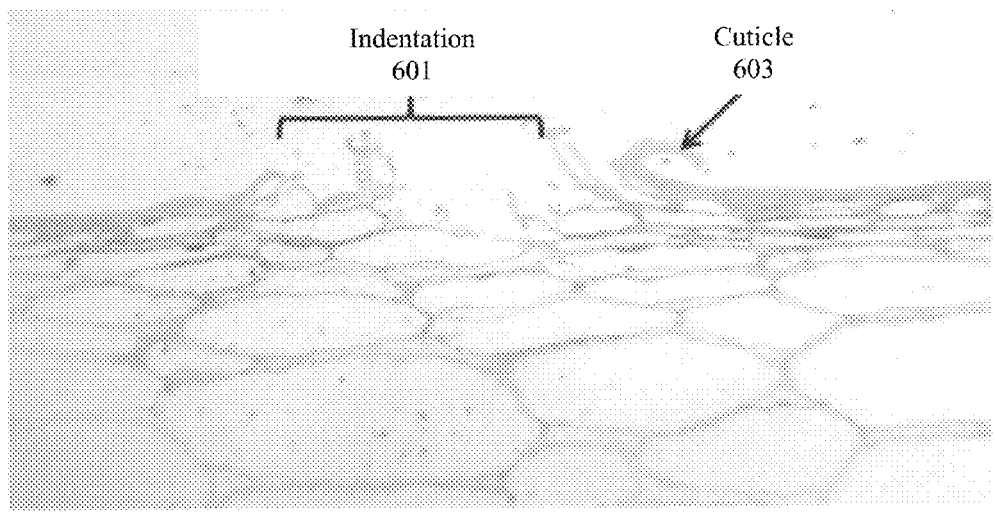
FIG. 6 is a side cross sectional view of a cuticle treated with light energy.

In an exemplary application of the methods disclosed herein, FIG. 6 shows a light energy applied to a leaf of a plant to create an indentation 601. Light energy can involve laser light technology, which uses low level light energy to disperse the cuticle 603 of a plant thereby creating microscopic indentations through cuticle 603. In doing so, infiltration of substances into the leaf is greatly enhanced, where they can be transported and absorbed by phloem cells. This is partially the result of the removal of the protective layers such as the cuticle (e.g., wax/cutin) on leaves and bark on stems. The indentation can be a laser generated pore of about 200 µm wide.

Light energy can be applied by using a single light beam to rupture the cuticle or bark. Additionally, light energy can comprise of a plurality of light beams that can rupture the cuticle in a number of locations to create a plurality of indentations. In typical embodiments, the light energy can be applied to the lower portion of the stem or of the bark in a similar manner as leaves. For example, light energy may be applied to a root or crown of a tree to create a superficial indentation. In another example, light energy can be applied to a flower or stem of a plant to create a superficial indentation.

Figure 7:
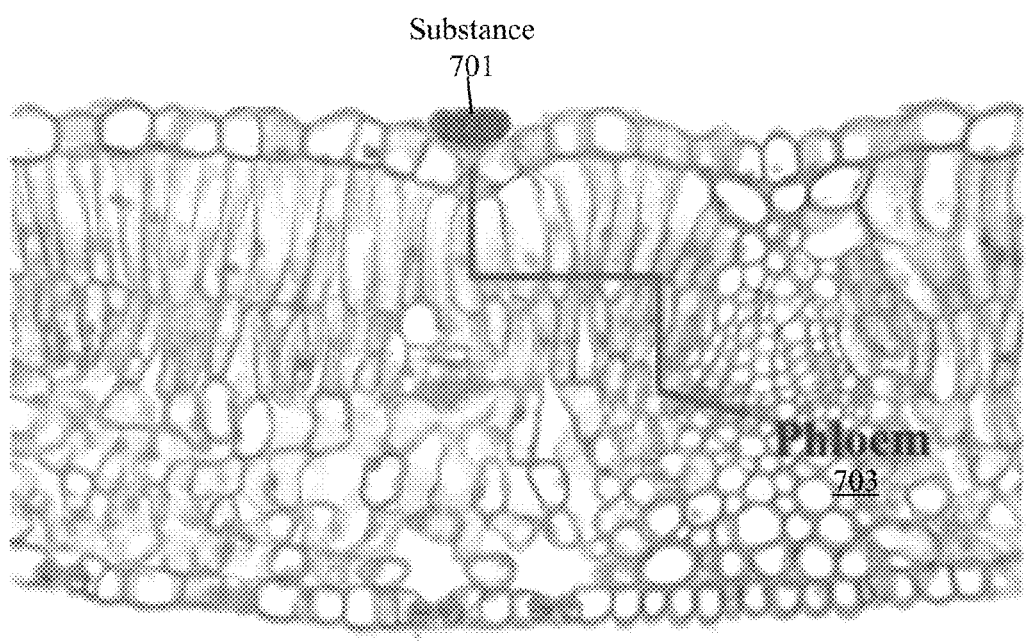
FIG. 7 is a side cross sectional view of an antimicrobial solution applied on an indentation.

It should be noted that by rupturing cuticle 603, a substance can be applied to the indentation. FIG. 7 represents a diagrammatic scheme of a cross section of a leaf showing an enhanced pathway of a substance 701 into phloem cells 703. The indentation allows for the penetration of substances into the leaf by bypassing the limited permeability of the cuticle or the bark. The substances then move through the cellulose fibers of the plant cell walls until reaching the phloem. Thus, once inside the leaf tissue, substances can follow the natural transport pathway through the apoplast, absorbed by phloem cells, and transported throughout the tree.

Therefore, and in a general aspect, a method is contemplated for delivering a compound to a living plant. In a first step, light energy is applied to a first portion of the plant to create a first indentation. In a second step, a first dosage of the compound is applied to the first indentation in an amount effective to induce a biological response.

To illustrate the effectiveness of the methods disclosed herein, a test substance was used to show the enhanced penetration through foliar application. Among test substances, phloem mobile compounds NBDG, a fluorescent analog of glucose (a natural sugar found in plants), and carboxyfluorescin-SE (a membrane permeable substance only fluorescent in live cells) were used in an experiment. Both substances were manually applied onto lased leaves (using a 13×39 dot indentation pattern 801) at a concentration of 5 mg/mL.

While the discussion below is related to using NBDG, it should be noted that results with carboxyfluorescin-SE were similar to those shown.

Figure 8A:
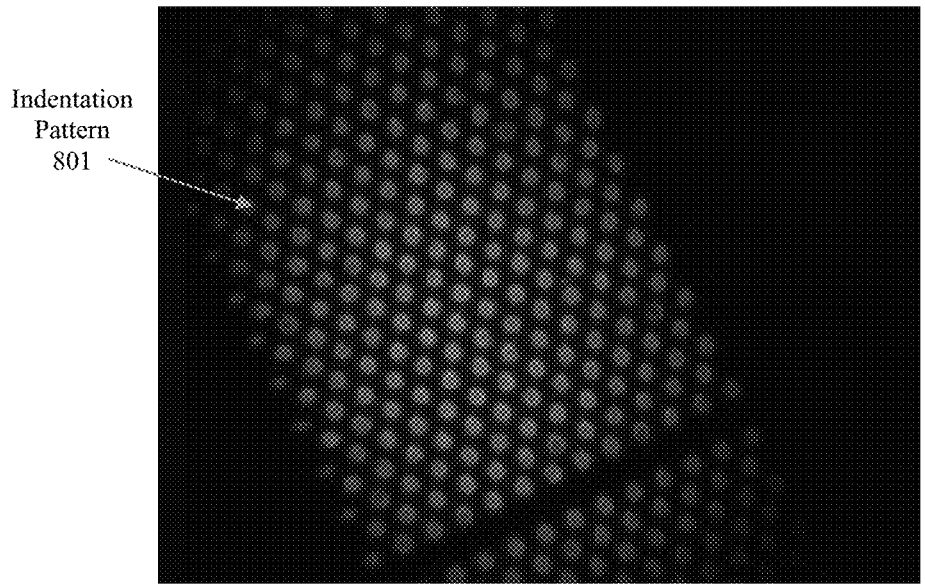
FIGS. 8A-8B are elevated views of a treated and untreated citrus leaf after being applied with light energy.
Figure 8B:
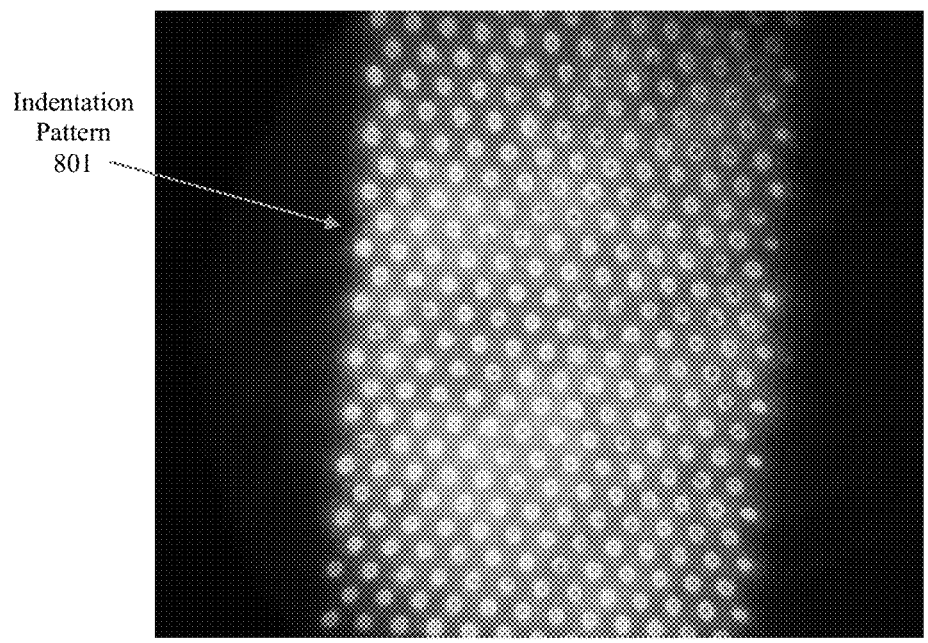

Uptake of these substances into the tested leaf was rapidly confirmed by the spread of fluorescence within the lased area (shown in FIG. 8B) as compared to lased leaves without applied solution (shown in FIG. 8A). Control leaves where NBDG was applied to the surface of un-lased leaves showed no fluorescence (dark field) indicating no uptake. FIGS. 8A-8B were observed under fluorescent microscopy and FIG. 8B was taken 10 minutes after the application of 5 µL of NBDG.

Figure 9A:
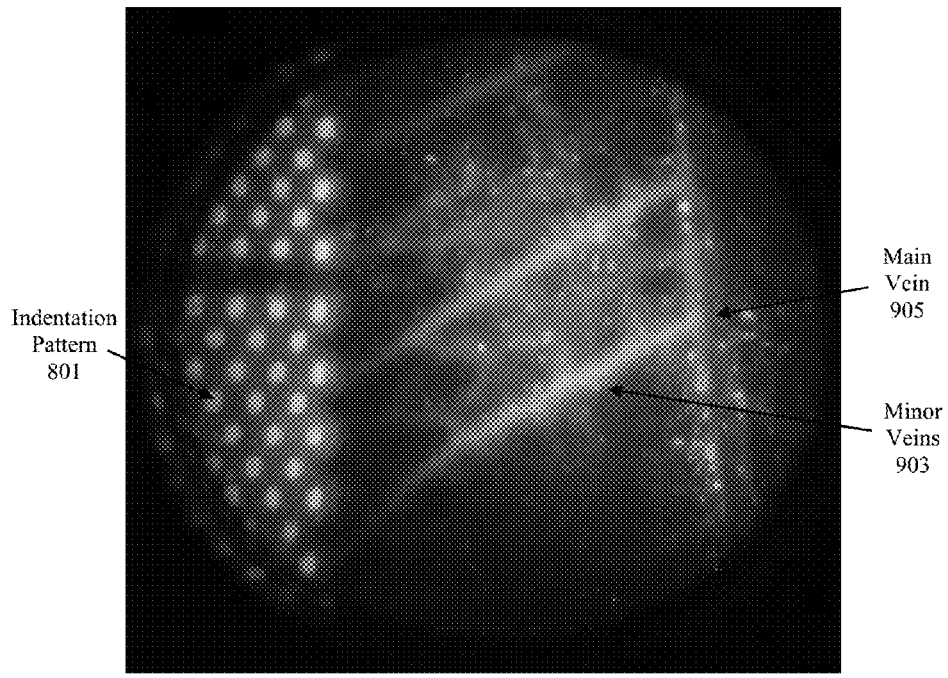
FIGS. 9A-9B are elevated views of a citrus leaf after showing uptake of phloem mobile compounds in the minor and major veins.
Figure 9B:
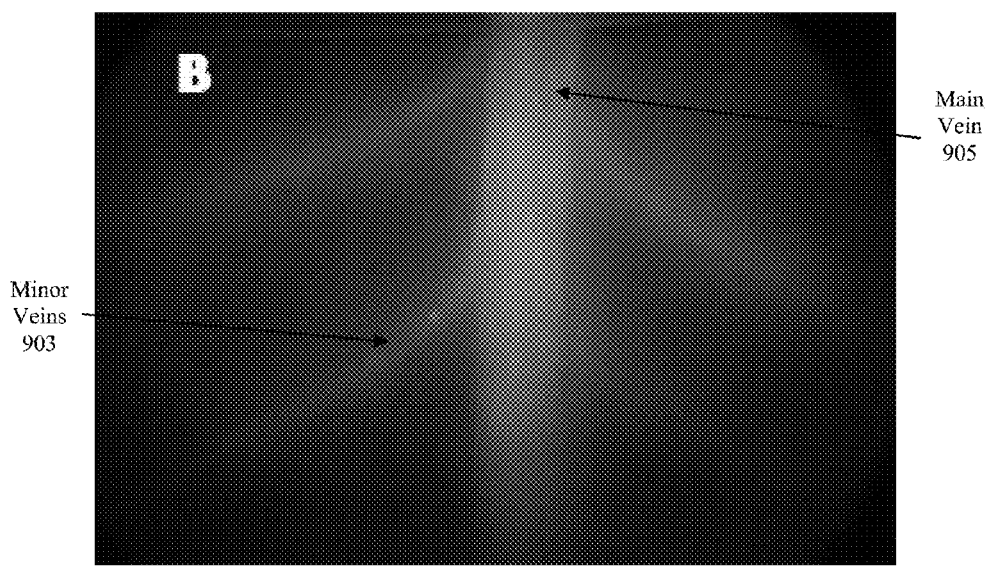

Within 2 h, fluorescent NBDG was observed within the lateral veins of the lased leaves (shown in FIGS. 9A-9B) emerging from the application area. FIGS. 9A-9B are fluorescent micrographs of a portion of a lased citrus leaf. FIG. 9A shows indentation pattern 801 on the lased leaf and movement of the NBDG in the minor veins 903 and main vein 905. FIG. 9B is another image showing the NBDG in a minor veins 903 and main vein 905.

Figure 10:
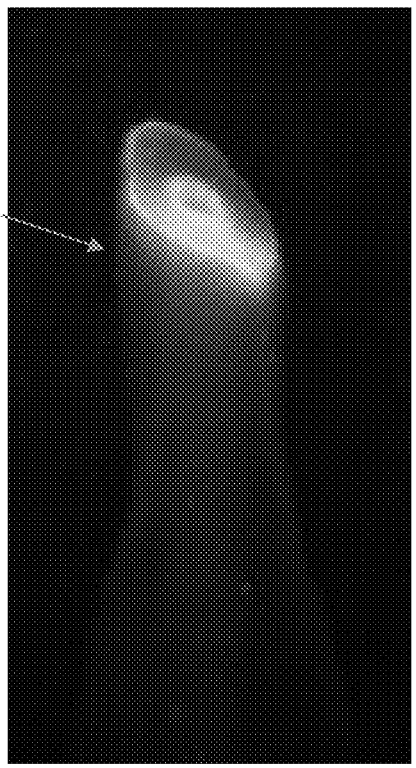
FIG. 10 is a cross sectional view of a petiole of a citrus leaf showing movement of phloem mobile compounds.

Four hours after application, NBDG had already reached and passed the base of the petiole 1001 as shown in FIG. 10. Thus, the above images demonstrate that (i) laser etching of the cuticle is an effective way to enhance penetration of applied substances, (ii) movement through photosynthetic tissue and into the phloem is not affected by the application method and (iii) applied phloem-mobile substances proceeded in a natural way.

Figure 11A:
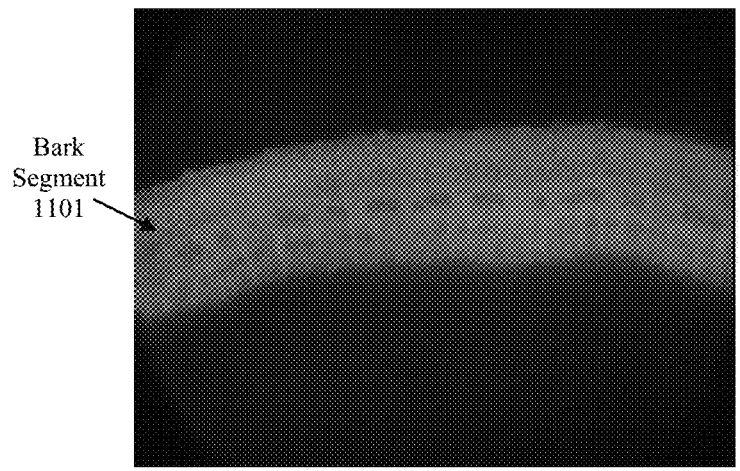
FIGS. 11A-11B are horizontal cross section views of bark from untreated control (A) and treated trees.
Figure 11B:
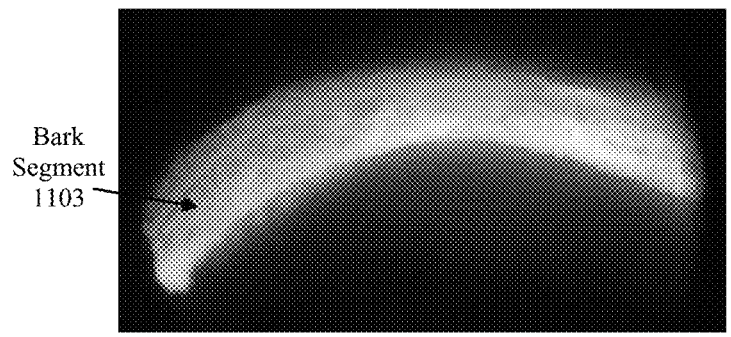

It should be appreciated that movement of the foliarly applied NBDG continued down the stem and towards the roots. Within 8 h, fluorescence from NBDG was observed in the phloem of bark tissue approximately 20 cm from the treated leaf. FIGS. 11A-11B show bark sections of young trees. FIG. 11A shows a control bark segment 1101 of an untreated tree. FIG. 11B shows a bark segment 1103 of a treated tree 8 hours after application of NBDG on lased leaves. The distance between the lased leaves and bark segment 1103 was approximately 20 cm.

Figure 12A:
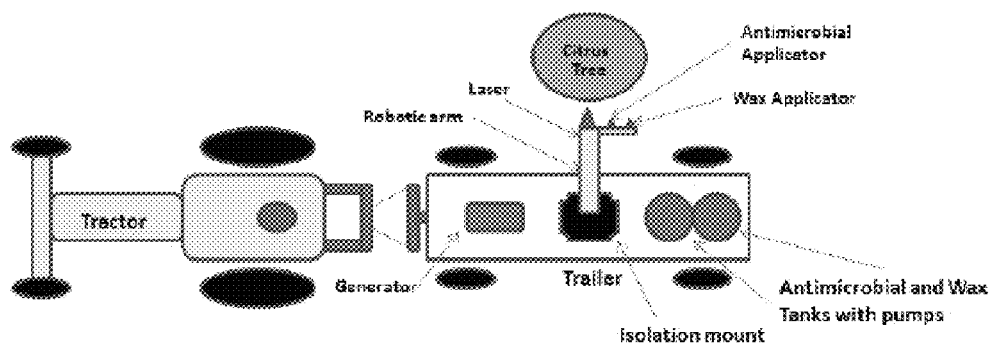
FIGS. 12A-12B is a top and perspective view of embodiments of an apparatus for delivering a substance to a plant.
Figure 12B:
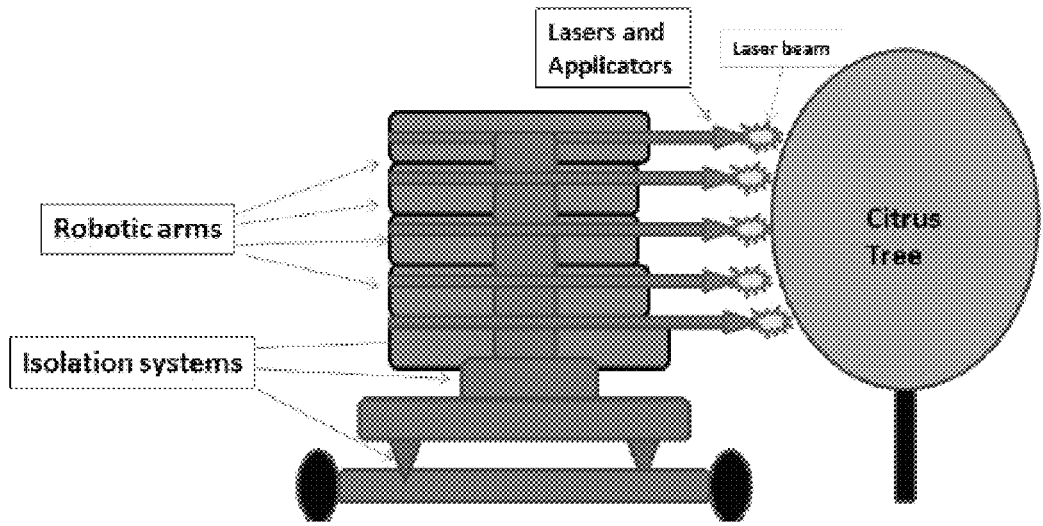

FIGS. 12A-12B shows an embodiment of an apparatus for delivering a substance to a plant. The basic unit comprises an electronically controlled robotic arm containing: (i) a laser light emitter to disperse a light to a treatment area or second site on a plant; (ii) a substance nozzle applicator; and (iii) a wax applicator to seal the treated area as shown in FIG. 12A. All these nozzles can be mounted at the end of an arm on a movable bracket. In sequence, the first nozzle can emit light energy to create a momentary breach in the treatment area or second site on the plant, the second nozzle can deliver the substance over the treatment area or second site on the plant, and the third nozzle can reseal the treatment area or second site on the plant as the system moves forward. The system design will reduce the amount of substance needed by applying it only over the treatment area or second site on the plant, and not over the entire canopy/area and also ensures that the indentations are sealed to protect against water loss and other pathogens.

The apparatus can further comprise five individual arms as shown in FIG. 12B, each independently controlled and electronically actuated. These arms are stacked vertically, with each laser having a scan window of approximately 14"×14". This will give a maximum laser treated height of approximately 6 ft. The design of the system is modular so that more laser arms can be added vertically to accommodate larger trees if needed. The entire apparatus will be mounted on a platform which will be pulled through the grove by a tractor at 2.3-2.7 mph. As the system moves down the grove, optics will guide each arm to determined positions on the canopy, avoiding entanglement with branches of uneven length.

Each independently controlled arm, with the laser system and attached applicator nozzle assembly, is designed to typically move in the horizontal direction. However, each laser system and assembly arm can move independently from the other arms. This independent scheme allows each laser system to follow the contour of the tree canopy in its scan path. Multiple sensors on the articulating arm and laser system will ensure that it traces the tree canopy. The entire laser system can also be raised or lowered vertically depending on tree height. In addition, because of tree canopy irregularities and differing tree height, sensors on the laser will turn it "off and on" based on the presence of canopy to be treated within its scan path. The laser system and applicator nozzles will be attached on the arm using a rotating mount. This rotating mount will allow the lasers to be pointed at an angle to the tree canopy to better laser the adaxial (top) of the leaves.

In such a harsh working environment, the trailer platform, on which the entire laser system is mounted on, can have an isolation design so that it will eliminate (as much as possible) the transfer of motion of the trailer as it moves through the grove. The horizontal articulating robotic arms will also have isolation mounts that are designed to minimize any further vibrations from affecting the operation of the laser system in the field. A generator and tanks with pumps can be mounted on the trailer, as shown in FIG. 12B. The generator provides sufficient power for the laser systems, pumps and associated electronic equipment. The tanks provide the storage for at least one of the substance and wax. The two pumps deliver the substance and wax to the applicator nozzles. The overall system design preferably takes into account environmental working conditions, heat, humidity, rain and varying grove conditions.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a plant having an infected site, comprising:
    applying a light energy to a treatment area on the plant to create a first indentation, wherein the treatment area is distal from the infected site;
    applying a first dosage of an antimicrobial substance to the treatment area in an amount effective to reduce a symptom of a pathogen in the infected site; and
    wherein the pathogen comprises Huanglongbing ("HLB").

2. The method of claim 1, wherein the applying the light energy includes creating an indentation pattern.

3. The method of claim 1, wherein the applying a light energy and the applying the first dosage is within a predetermined time.

4. The method of claim 1, wherein the infected site is in a phloem.

5. The method of claim 4, wherein the treatment area is a surface of at least one of a leaf, a stem and a bark.

6. The method of claim 4, wherein the first indentation is a rupture of a cuticle on the leaf.

7. The method of claim 1, wherein the applying the light energy further comprises creating a second indentation.

8. The method of claim 1, further comprises applying a wax to the treatment area in an amount effective to seal the first indentation after the applying the light energy to the treatment area and the applying the first dosage of the substance to the treatment area.

9. The method of claim 1, wherein the first indentation has a diameter of approximately 100-300 µm.

10. The method of claim 1, wherein the plant is a citrus tree.

11. The method of claim 1, wherein the treatment area and the infected site are in distinct plant systems.

12. A method of delivering a first substance to a first site in a plant having Huanglongbing ("HLB"), comprising:
- applying a light energy to a second site located on a plant surface to create a first disruption wherein the first site and the second site are different in kind;
- applying a first dosage of the first substance to the second site in an amount effective to promote uptake of the first substance to the first site via the first disruption; and
- wherein the first dosage and first disruption are sufficient to achieve a biological response effective to reduce a symptom of HLB.

13. The method of claim 12, wherein the first substance comprises an antimicrobial.

14. The method of claim 12, further comprises applying an antifungal spray to the second site.

15. The method of claim 12, wherein the plant comprises at least one of a tree, a row crop, a bush crop and an ornamental plant.

16. The method of claim 12, further comprises applying a wax to the second site in an amount effective to seal the first disruption after the applying the light energy to the second site and the applying the first dosage of the substance to the second site.

17. The method of claim 12, further comprises applying a second dosage of either the first substance or a second substance, wherein the second substance comprises at least one of an antimicrobial, a pesticide, a fertilizer, an herbicide and a fungicide.

18. The method of claim 12, wherein the first site comprises a cuticle and the second site comprises at least one of a xylem and a phloem.

19. A method of delivering a compound to a living plant having Huanglongbing ("HLB") to treat the living plant, comprising:
- applying a light energy to a first portion of the plant to create a first indentation;
- applying the light energy to a second portion of the plant to create a second indentation; and
- applying a first dosage of the compound to at least one of the first indentation and the second indentation in an amount effective to induce a biological response effective to reduce a symptom of HLB; and
- wherein the first portion is disposed on at least one of a leaf, stem, and a bark and the second portion is disposed on a different one of the leaf, stem, and the bark.

20. The method of claim 19, further comprises applying a wax to the first indentation after the compound is applied.

* * * * *